United States Patent
Draper et al.

(10) Patent No.: US 10,406,293 B2
(45) Date of Patent: Sep. 10, 2019

(54) ASSEMBLY FOR A DRUG DELIVERY DEVICE COMPRISING A FEEDBACK FEATURE

(71) Applicant: Sanofi-Aventis Deutschland GmbH, Frankfurt am Main (DE)

(72) Inventors: Paul Richard Draper, Worcestershire (GB); Paul Griffin, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 590 days.

(21) Appl. No.: 14/774,692

(22) PCT Filed: Mar. 10, 2014

(86) PCT No.: PCT/EP2014/054535
§ 371 (c)(1),
(2) Date: Sep. 10, 2015

(87) PCT Pub. No.: WO2014/139922
PCT Pub. Date: Sep. 18, 2014

(65) Prior Publication Data
US 2016/0030675 A1    Feb. 4, 2016

(30) Foreign Application Priority Data
Mar. 13, 2013 (EP) .................... 13159057

(51) Int. Cl.
*A61M 5/315* (2006.01)

(52) U.S. Cl.
CPC ....... *A61M 5/3157* (2013.01); *A61M 5/31551* (2013.01); *A61M 5/31585* (2013.01); *A61M 2205/581* (2013.01); *A61M 2205/582* (2013.01)

(58) Field of Classification Search
CPC .............. A61M 2205/581–582; A61M 5/3157
See application file for complete search history.

(56) References Cited

U.S. PATENT DOCUMENTS

| | | | |
|---|---|---|---|
| 533,575 A | 2/1895 | Wilkens | |
| 4,201,209 A * | 5/1980 | LeVeen | A61M 5/31511 222/386 |
| 4,865,591 A | 9/1989 | Sams | |
| 5,092,842 A | 3/1992 | Bechtold et al. | |
| 5,226,895 A | 7/1993 | Harris | |

(Continued)

FOREIGN PATENT DOCUMENTS

| | | |
|---|---|---|
| CA | 2138528 | 12/1998 |
| CA | 2359375 A1 | 7/2000 |

(Continued)

OTHER PUBLICATIONS

Communication Pursuant to Rule 114(2) EPC issued in European Patent Application No. 14708566.6 dated Oct. 24, 2016.

(Continued)

*Primary Examiner* — Edelmira Bosques
(74) *Attorney, Agent, or Firm* — Fish & Richardson P.C.

(57) ABSTRACT

An assembly for a drug delivery device is provided, the assembly comprising at least one feedback feature. The feedback feature is configured to indicate the end of a dispense operation to a user by giving an audible and/or tactile feedback.

13 Claims, 7 Drawing Sheets

(56) References Cited

U.S. PATENT DOCUMENTS

| | | |
|---|---|---|
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber et al. |
| 5,383,865 A | 1/1995 | Michel |
| 5,391,157 A | 2/1995 | Harris et al. |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,807,346 A | 9/1998 | Frezza |
| 5,820,602 A | 10/1998 | Kovelman et al. |
| 5,851,079 A | 12/1998 | Horstman et al. |
| 5,921,966 A | 7/1999 | Bendek et al. |
| 5,957,896 A | 9/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman et al. |
| 6,613,023 B2 | 9/2003 | Kirchhofer et al. |
| 6,699,224 B2 | 3/2004 | Kirchhofer et al. |
| 6,899,698 B2 | 5/2005 | Sams |
| 6,932,794 B2 | 8/2005 | Giambattista et al. |
| 6,936,032 B1 | 8/2005 | Bush, Jr. et al. |
| 7,169,132 B2 | 1/2007 | Bendek et al. |
| 7,241,278 B2 | 7/2007 | Moller |
| 7,427,275 B2 | 9/2008 | DeRuntz et al. |
| 7,678,084 B2 | 3/2010 | Judson et al. |
| 7,850,662 B2 | 12/2010 | Veasey et al. |
| 8,186,233 B2 | 5/2012 | Joung et al. |
| 2002/0052578 A1 | 5/2002 | Moller |
| 2002/0120235 A1 | 8/2002 | Enggaard |
| 2002/0179461 A1* | 12/2002 | Mollstam ........... B65D 47/2031 206/222 |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0016143 A1 | 1/2007 | Miller et al. |
| 2009/0012479 A1 | 1/2009 | Moller et al. |
| 2009/0275916 A1 | 11/2009 | Harms et al. |
| 2010/0002135 A1* | 1/2010 | Dodd .................. G09B 21/006 348/553 |
| 2011/0192735 A1* | 8/2011 | Cronin ................ B65D 47/243 206/222 |
| 2012/0271125 A1* | 10/2012 | Bernstein ......... A61B 5/150022 600/309 |

FOREIGN PATENT DOCUMENTS

| | | |
|---|---|---|
| CN | 102665805 | 9/2012 |
| EP | 0496141 A1 | 7/1992 |
| EP | 0594357 A1 | 4/1994 |
| EP | 0897729 A2 | 2/1999 |
| EP | 0937471 A2 | 8/1999 |
| EP | 0937476 A2 | 8/1999 |
| EP | 1776975 A2 | 4/2007 |
| JP | 2008-142502 | 6/2008 |
| WO | 9307922 A1 | 4/1993 |
| WO | 9324160 A1 | 12/1993 |
| WO | 9938554 A1 | 8/1999 |
| WO | 0110484 A1 | 2/2001 |
| WO | 0230495 A2 | 4/2002 |
| WO | 02092153 A2 | 11/2002 |
| WO | 03080160 A1 | 10/2003 |
| WO | 2006084876 A1 | 8/2006 |
| WO | 2009039851 A1 | 4/2009 |
| WO | WO2010112565 A1 * | 10/2010 |
| WO | 2011043714 A1 | 4/2011 |
| WO | WO 2011/047298 | 4/2011 |
| WO | WO 2012/085584 | 6/2012 |
| WO | WO 2012/110577 | 8/2012 |

OTHER PUBLICATIONS

"Pen-injectors for medical use—Part 1: Pen-injectors—Requirements and test methods," International Standard, reference No. ISO 11608-1:2000(E), first edition Dec. 15, 2000, 32 pages.

International Preliminary Report on Patentability in International Application No. PCT/EP2014/054535, dated Sep. 15, 2015, 7 pages.

International Search Report and Written Opinion in International Application No. PCT/EP2014/054535, dated May 9, 2014, 9 pages.

* cited by examiner

ASSEMBLY FOR A DRUG DELIVERY DEVICE COMPRISING A FEEDBACK FEATURE

CROSS REFERENCE TO RELATED APPLICATIONS

The present application is a U.S. National Phase Application pursuant to 35 U.S.C. § 371 of International Application No. PCT/EP2014/054535 filed Mar. 10, 2014, which claims priority to European Patent Application No. 13159057.2 filed Mar. 13, 2013. The entire disclosure contents of these applications are herewith incorporated by reference into the present application.

FIELD OF INVENTION

The present disclosure relates to an assembly for a drug delivery device. The assembly comprises a feedback feature.

BACKGROUND

It is an object of the present invention to provide an assembly for a drug delivery device having improved properties.

An assembly for a drug delivery device is provided, the assembly comprising at least one feedback feature. The feedback feature may be configured to indicate the end of a dispense operation to a user by giving an audible and/or tactile feedback. The audible feedback may be, for example, an audible click. The tactile feedback may be, for example, an impact on the skin of a user, in particular on a user's finger. Alternatively, the tactile feedback may be a vibration of a part of the assembly. In particular, the feedback may be a well-defined signal. In particular, the feedback may indicate to a user that the actuator may be released and the device may be withdrawn from a user's skin.

The advantage of a feedback feature being configured to indicate the end of a dispense operation is that a clear indication is given to a user when a dispense operation has been completed. Thereby, the use of the drug delivery device may be easy for a user. Furthermore, the dosing accuracy of a drug delivery device may be increased. In particular, it may be inhibited that a user interrupts a dispense operation, for example by withdrawing the drug delivery device from the skin, before a complete dose has been delivered. Furthermore, such a feedback provides an additional benefit for visually impaired users.

SUMMARY

According to one embodiment, the assembly comprises an actuator which is configured to be operated by a user in order to dispense a dose. A feedback may be created when the actuator reaches an end position at the end of a dispense operation. The end position of the actuator may be a most distal position of the actuator. The term "most distal position" may describe a position of a part of the assembly which is closest to a dispensing end of the drug delivery device. In particular, the actuator may be in its end position when it is fully depressed into the drug delivery device. The actuator may be configured as a button. According to one embodiment, the feedback may be created when the actuator is close to its end position.

According to one embodiment, the at least one feedback feature comprises at least one snap feature which is configured to snap through when it is compressed above a certain load, thereby giving a feedback to a user. Thereby, the snap feature may produce an audible signal. In particular, the snap feature is configured to snap through at the end of a dispense operation. In particular, the snap feature is configured to snap through when the actuator reaches its end position. Initially during compression of the snap feature, the stiffness of the snap feature may remain fairly constant. At a certain point, the stiffness of the snap feature may reduce significantly. Thereby, the force required to cause a further deflection of the snap feature may decrease. This may cause the snap-through behaviour of the snap feature. The snap feature may relax to its initial shape after the dispense operation, in particular when the snap feature is not compressed anymore. When the snap feature relaxes, it may produce a further audible signal.

According to one embodiment, the feedback feature, in particular the snap feature may comprise the shape of a dome. In particular, the feedback feature may comprise the shape of an arched disk. In one embodiment, the feedback feature comprises at least one recess. The recess may be, for example, a concave cut out. Due to the at least one recess, the feedback feature may comprise a sufficient flexibility. Thereby, the feedback feature may be configured to snap through when it is compressed above a certain load. In particular, the size and shape of the recess may influence the force which is necessary to cause the feedback feature to snap through. In a further embodiment, the snap feature may be free of any recess. Thereby, the feedback signal may be more distinct.

According to one embodiment, the at least one feedback feature comprises a metal material. Alternatively, the at least one feedback feature may comprise a plastic material. Preferably, the feedback feature comprises a resilient material.

According to one embodiment, the assembly comprises a member which is configured to interact with the feedback feature. The member may be configured to axially move, in particular when it does not interact with the feedback feature. For example, the member is configured to axially move during an initial phase of a dispense operation. The interaction of the axially moveable member with the feedback feature may cause the feedback. The axially moveable member may be a sleeve member.

According to one embodiment, the feedback feature may be configured to be compressed between two parts of the assembly. For example, the feedback feature may be compressed between the actuator and the axially moveable member. Alternatively, the feedback feature could be compressed between the housing and the driver.

According to one embodiment, the member may axially move with respect to a housing of the drug delivery device between two stops at least during the setting of a dose. During the dispensing of a dose, in particular when the actuator approaches its end position, the member may be temporarily restrained between these two stops. Thereby, the member may be temporarily axially fixed. In particular, the member may be axially fixed when it interacts with the feedback feature, i. e. when the actuator contacts the feedback feature.

According to one embodiment, the actuator interacts with the feedback feature, in particular with the snap feature. In particular, the actuator may interact with the feedback feature during a dispense operation. The feedback feature, in particular the snap feature, may be arranged between the actuator and the axially moveable member. When the actuator approaches its end position during a dispense operation, the feedback feature may be clamped between the actuator and the axially moveable member. When the actuator is further moved towards the axially moveable member, the feedback feature may be compressed by the actuator. In particular, the force on the feedback feature increases when the actuator is further moved towards the other part. In particular, the actuator may exert a force on the feedback feature during a dispense operation.

According to one embodiment, the assembly may comprise an enhancement feature being configured to enhance the feedback of the feedback feature. In particular, the volume of an audible feedback may be increased. Additionally or alternatively, a tactile feedback may be enhanced. Furthermore, an audible feedback may be enhanced by an additional tactile feedback or vice versa. According to one embodiment, the enhancement feature may be attached to the axially moveable member. In particular, the enhancement feature may be an integral part of the axially moveable member. For example, the enhancement feature may be a protrusion of the axially moveable member. Alternatively, the enhancement feature may comprise a flexible section, in particular a flexible section of the axially moveable member. In an alternative embodiment, the enhancement feature may be attached to another part of the assembly, for example to a housing.

According to one embodiment, the member interacting with the feedback feature, in particular the axially moveable member, comprises a rigid section and a flexible section. The flexible section of the member may be configured to be compressed during the dispense operation. In particular, the flexible section may be compressed at the beginning of an interaction of the axially moveable member with the feedback feature, in particular with the snap feature. According to an alternative embodiment, the flexible section may be located at a fixed part of the drug delivery device, for example at a housing.

According to one embodiment, the axially moveable member is configured to expand in an axial direction when the feedback feature, in particular the snap feature snaps through. In particular, the flexible section may expand in an axial direction when the snap feature snaps through. In particular, the flexible section may be configured to expand in a direction towards a proximal end of the device. The proximal end may be an end which is furthest away from a dispensing end of the device. Thereby, the axially moveable member may further compress the snap feature. Due to the flexible section, the axially moveable member may act as a spring member. Due to the elastic energy stored in the flexible section and in the snap feature, and due to the low mass of these elements, a resulting feedback may be louder and more energetic than with a fully rigid member interacting with the feedback feature. In particular, due to the enhancement feature, the stiffness of the contact constraints on the feedback feature may be reduced. The contact constrains may be constraints which limit a movement of the feedback feature. Furthermore, due to the enhancement feature, in particular due to flexibility of the axially moveable member, the feedback feature may vibrate with a larger amplitude and for a longer duration, because of a reduced energy transmission of the feedback feature to the contacting components.

According to one embodiment, the flexible section comprises at least one opening. The opening may be located in a side wall of the axially moveable member. Due to the at least one opening, the flexibility of the flexible section may be achieved.

According to one embodiment, the feedback feature comprises an opening, wherein at least one element of the assembly extends through the opening. For example, the actuator may extend through the opening.

According to one embodiment, the at least one feedback feature comprises at least one tactile feature which is configured to give a tactile feedback to a user at the end of a dispense operation. The tactile feature may be configured as an enhancement feature. In particular, a tactile feedback may be given by the tactile feature in addition to an audible feedback given by the feedback feature or given by a further feedback feature. Furthermore, a tactile feedback which may be given to a user for example due to a snap-through of the snap feature may be enhanced. For example, a tactile feedback which derives from a vibration of the snap feature may be enhanced by a tactile feature which may directly contact a user's skin. The advantage of a feedback feature which gives a tactile feedback is that a clear feedback may be given to a user, even in a noisy environment, or to a user with impaired hearing.

According to one embodiment, the at least one tactile feature is configured to protrude from the actuator at the end of a dispense operation.

According to one embodiment, the at least one tactile feature is configured to protrude through an opening at the end of a dispense operation. In particular, the opening may be located in the actuator. By protruding through the opening, the tactile feature may get in contact with the skin of a user. Thereby, a tactile feedback may be given to a user.

According to one embodiment, the feedback feature comprises a snap feature, wherein the at least one tactile feature snaps out when the snap feature snaps through. In particular, the snapping through of the snap feature may cause a fast and well-defined movement of the tactile feature with respect to the actuator. According to one embodiment, the tactile feature may be axially fixed at the end of a dispense operation, and the actuator may move towards the distal end of the device, thereby causing the tactile feature to snap out. According to a further embodiment, the tactile feature may move towards the proximal end of the device while the actuator moves towards the distal end of the device at the end of a dispense operation. Thereby, the speed with which the tactile feature snaps out may be increased. This may lead to a stronger tactile signal. The snap feature may create an audible and tactile feedback. The feedback of the snap feature may be enhanced by the tactile feature.

According to one embodiment, the at least one tactile feature may be attached to the member interacting with the feedback feature, in particular to the axially moveable member. In particular, the tactile feature comprises the shape of an arm, which may extend from the moveable member. In one embodiment, the assembly may comprise a plurality of tactile features, for example three. The tactile features may be arranged circumferentially around the member. According to one embodiment, the at least one tactile feature extends from the member in a proximal direction.

Furthermore, a drug delivery device is provided, the drug delivery device comprising an assembly which is configured as previously described. In particular, the drug delivery device may comprise a feedback feature, which is configured to indicate an end of a dispense operation to a user by giving an audible and/or tactile feedback.

The drug delivery device may be an injection device. The drug delivery device may be a pen-type device. The drug delivery device may be a variable dose device such that a user can select the size of a dose. The drug delivery device may be configured for multiple dose applications. The medication may be delivered to a user by means of a needle. The device may be delivered to a user in a fully assembled condition ready for use. The drug delivery device may be a disposable device. The term "disposable" means that the drug delivery device cannot be reused after an available amount of medication has been delivered from the drug delivery device. The drug delivery device may be configured to deliver a liquid medication. The medication may be, for example, insulin.

The term "medication", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5 des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-(Lys)6-NH2,
H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (02)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof An example of a pharmaceutically acceptable salt of a poly-sulphated low molecular weight heparin is enoxaparin sodium.

Antibodies are globular plasma proteins (~150 kDa http://en.wikipedia.org/wiki/Dalton%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains.

The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17.ed.Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

Further features, refinements and expediencies become apparent from the following description of the exemplary embodiments in connection with the figures.

DETAILED DESCRIPTION

Figure 1:
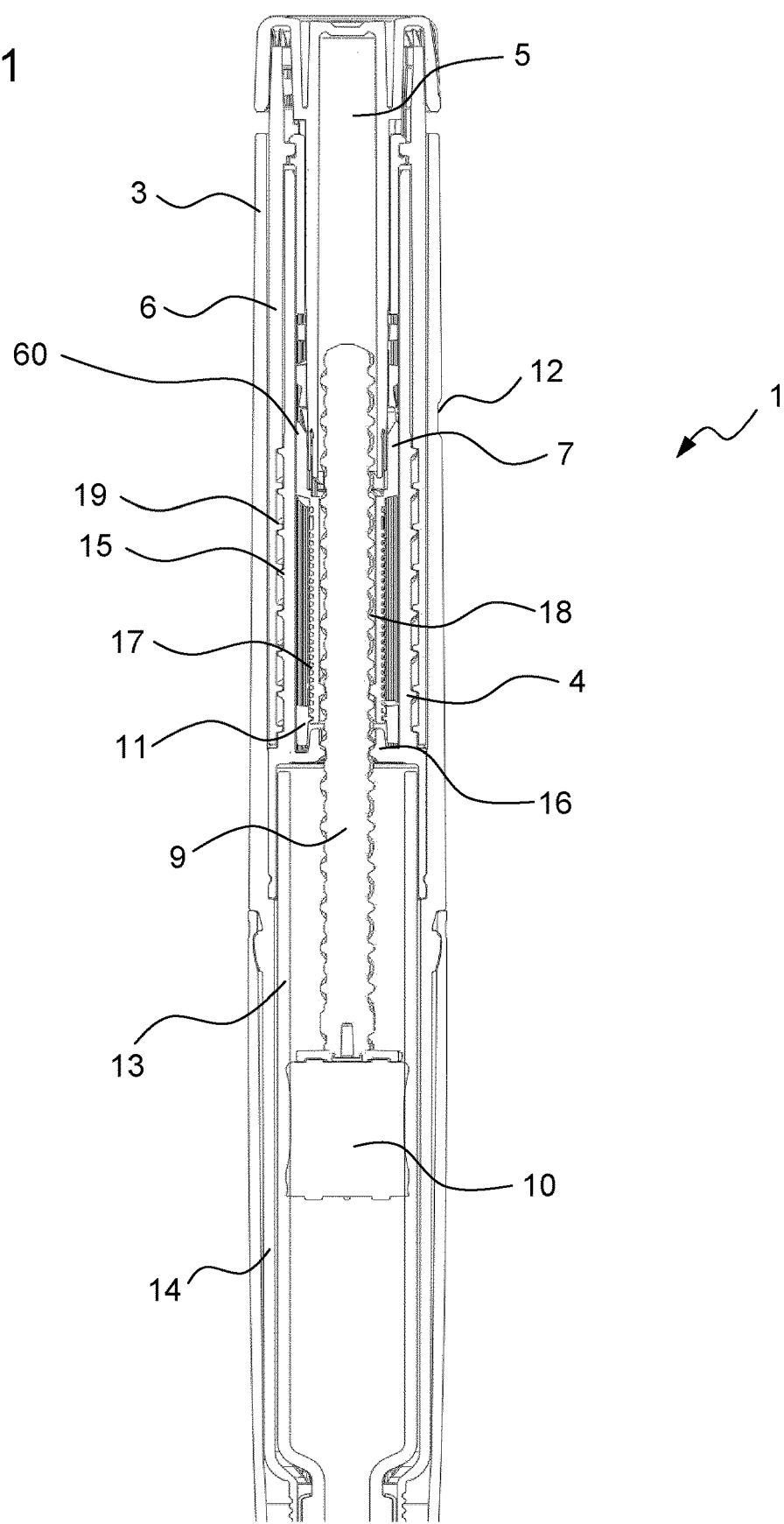
FIG. 1 shows a sectional view of a drug delivery device.

FIG. 1 shows a drug delivery device 1. In particular, the drug delivery device 1 is an injection device. The drug delivery device 1 is a variable dose device such that a user can select the size of a dose. The drug delivery device 1 is configured for multiple dose applications. The device can be delivered to a user in a fully assembled condition ready for use. The device has a low part count and is particularly attractive for cost-sensitive device applications.

The drug delivery device 1 comprises a housing 3, an inner body 4, an actuator 5, an indicator 6, a driver 7, a piston rod 9, a piston 10, a last dose stop 11, and a cartridge 13. A needle arrangement comprising a needle hub and a needle cover may be provided as additional components.

The housing 3 is a generally tubular element. A distal part of the housing 3 forms a cartridge holder 14 for receiving the cartridge 13.

The inner body 4 is a generally tubular element. The inner body 4 is received in the housing 3 and is permanently fixed therein to prevent any relative movement of the inner body 4 with respect to the housing 3. An external thread 15 is provided on the outer surface of the inner body 4. At its distal end, the inner body 4 comprises a further thread 16.

The actuator 5 is configured as a button. The actuator 5 is rotationally and axially moveable with respect to the housing 3 and the inner body 4. The actuator 5 is arranged at a proximal end of the drug delivery device 1. The actuator 5 is configured to be operated in order to dispense a dose of medication.

The indicator 6 is a generally tubular element. In particular, the indicator 6 is configured as a rotation member 43. In particular, the indicator 6 is configured to rotate with respect to the housing 3 during the setting and the dispensing of a dose. The indicator 6 is arranged concentrically around the inner body 4. In particular, the indicator 6 comprises an internal thread 19 engaging with the external thread 15 of the inner body 4. Thus, the indicator 6 is arranged between the inner body 4 and the housing 3. A series of numbers is provided, e.g. printed, on the outer surface of the indicator 6. The numbers are arranged on a helical line such that only one number or only a few numbers are visible through a window 12 of the housing 3. The numbers indicate the amount of a set dose. At the end of a dose dispense operation, the indicator 6 may have returned in its initial position, thereby indicating the end of a dispense operation to a user.

The piston rod 9 is configured as a lead screw. In particular, the piston rod 9 comprises two counter-handed threads which overlap each other. One of the threads of the piston rod 9 engages with the inner thread 16 of the inner body 4.

The driver 7 is a generally tubular element. An inner surface of the driver 7 has an inner thread 18 engaging with one of the external threads of the piston rod 9. The driver 7 is at least partly located within the inner body 4. A distal region of the driver 7 has an external thread 17. The driver 7 is configured to rotate and axially move with respect to the housing 3 during the setting of a dose. During the dispensing of a dose, the driver 7 is axially moveable and rotationally fixed with respect to the housing 3.

The last dose stop 11 is provided between the inner body 4 and the driver 7. An internal thread of the last dose stop 11 engages with the external thread 17 of the driver 7. The last dose stop 11 is configured to inhibit the setting of a dose which is larger than an amount of medication remaining in the cartridge 13. This is achieved by the last dose stop 11 abutting an abutment feature of the driver 7 when a dose is set which corresponds to an amount of medication remaining in the cartridge 13. The last dose stop 11 is configured as a nut.

In order to set a dose, the actuator 5 is rotated by a user. During the setting of a dose, the indicator 6 and the driver 7 are rotationally fixed with respect to the actuator 5. Thereby, the actuator 5, the indicator 6 and the driver 7 are rotated out of the housing 3. Thereby, the driver 7 is rotated along the piston rod 9 in a proximal direction, while the piston rod 9 is axially and rotationally fixed with respect to the housing 3 during the setting of a dose. The indicator 6 is rotated along the thread 15 of the inner body 4.

In order to dispense a dose, the actuator 5 is operated by a user. In particular, the actuator 5 is pushed in a direction towards a dispensing end of the device. During the dispensing of a dose, the actuator 5 and the driver 7 are rotationally fixed with respect to each other. The indicator 6 may rotate with respect to the actuator 5 and the driver 6 during the dispensing of a dose. Thereby, the indicator 6 may rotate back to its initial position and indicate the end of the dispense operation to a user. When the actuator 5 is operated, the driver 7 is also moved in a direction towards a dispensing end of the device. Thereby, the piston rod 9 is axially moved in a distal direction in order to dispense a dose of medication. In particular, the piston rod 9 is configured to rotate and axially move during the dispensing of a dose. When the actuator 5 has been operated and reached an end position, a feedback is given to a user. In particular, the feedback may indicate the end of a dispense operation. The end position of the actuator 5 may be its most distal position. In particular, the actuator 5 is in its end position when it is fully depressed.

In FIGS. 2 to 7, different embodiments of a feedback feature 2 are shown, which may indicate an end of a dispense operation to a user. In particular, FIGS. 2 and 5 to 7 show different assemblies 60 for a drug delivery device 1 comprising different embodiments of a feedback feature 2. The embodiments are illustrated in the context of a drug delivery device 1 as shown in FIG. 1, but are not limited thereon. In particular, the feedback feature 2 may also be used in a reusable device or in a device having a different drive mechanism.

Figure 2:
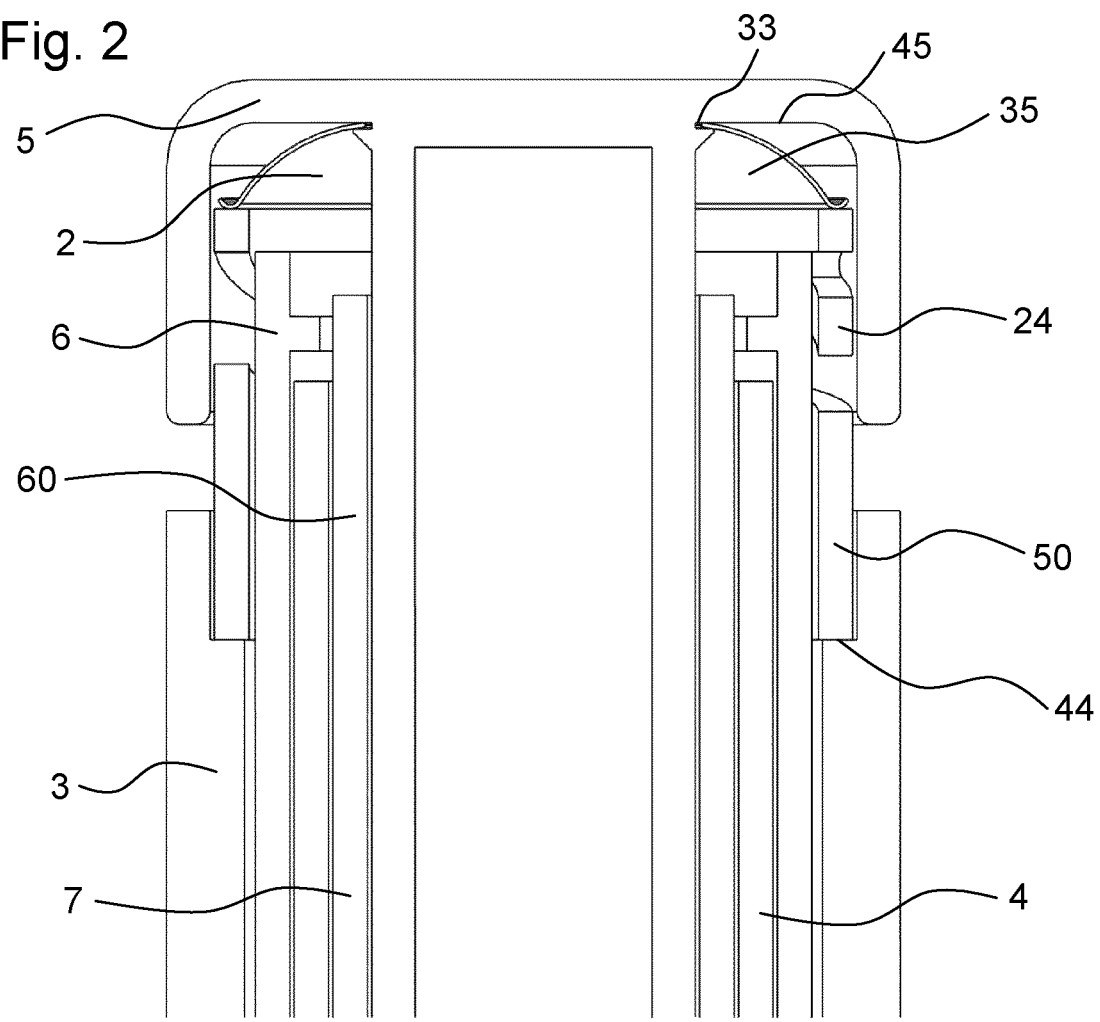
FIG. 2 shows a proximal section of a drug delivery device.

FIG. 2 shows a proximal section of a drug delivery device 1 comprising a feedback feature 2. The feedback feature 2 comprises a snap feature 35. The snap feature 35 is configured as a snap dome. The snap feature 35 comprises an opening 33, wherein the actuator 5 extends through the opening 33.

Figure 3A:
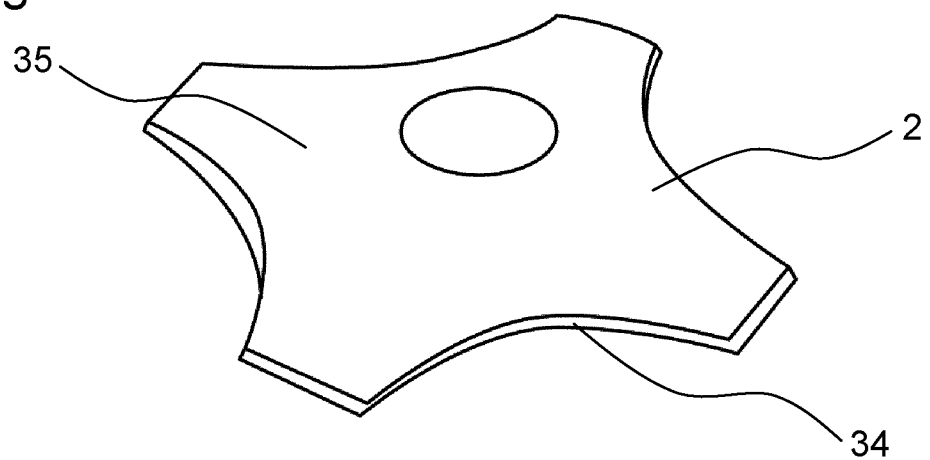
FIG. 3A shows a snap feature.

A snap feature 35 is shown in FIG. 3A. The snap feature 35 comprises or consists of a metal material. The snap feature 35 is configured as an arched disc. Furthermore, the snap feature 35 comprises at least one recess 34. The recess 34 is configured as a concave cavity. In particular, the snap feature 35 comprises four recesses 34. Due to the recesses 34, the snap feature 35 comprises a sufficient flexibility. The snap feature 35 is configured to snap through when it is compressed above a certain load. Thereby, the snap feature 35 creates an audible click. In particular, an audible and tactile feedback may be provided to a user at the end of a dispense operation.

Figure 3B:
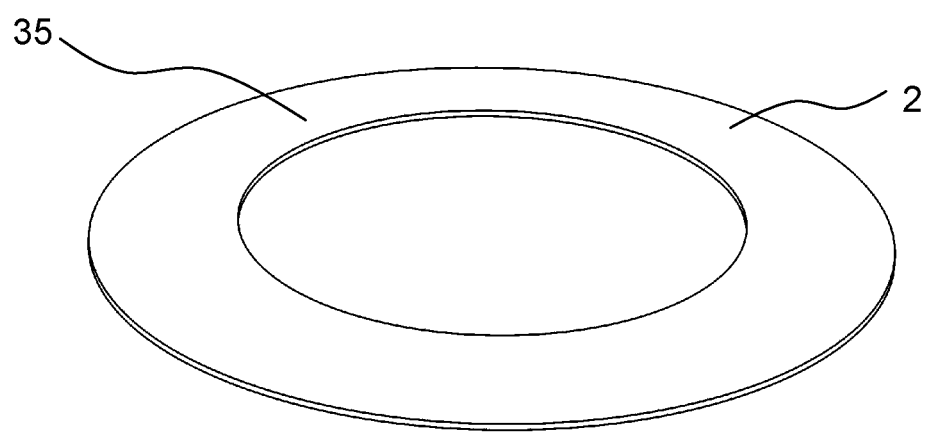
FIG. 3B shows a further embodiment of a snap feature.

In an alternative embodiment as shown in FIG. 3B, the snap feature 35 is configured as an arched disc which is free of any recess. Thereby, the snap feature 35 may comprise a high stiffness. Thereby, the feedback signal may be more distinct. In particular, the snap feature 35 is configured as an arched ring. In particular, the snap feature 35 comprises an opening.

Figure 4:
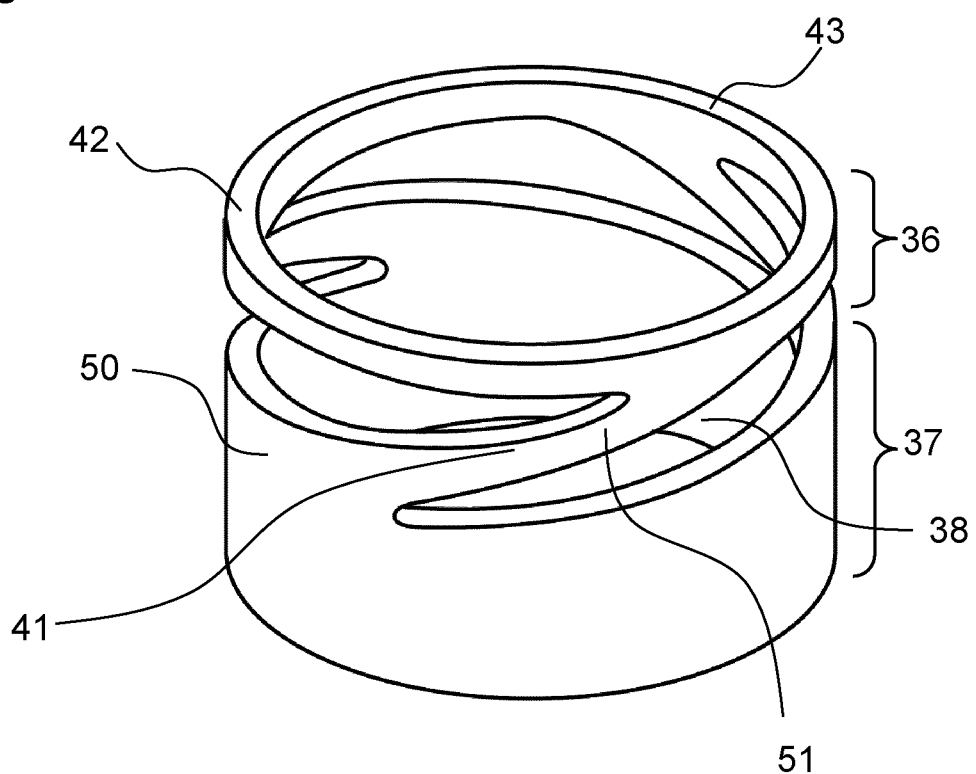
FIG. 4 shows an axially moveable member.

As illustrated in FIG. 2, the snap feature 35 is operated by an axially moveable member 50 as shown in FIG. 4. In particular, the axially moveable member 50 is a sleeve member 24. The sleeve member 24 is arranged between the actuator 5 and the indicator 6. The sleeve member 24 can move axially relative to the actuator 5 between two stops 44, 45. The snap feature 35 pushes apart the actuator 5 and the sleeve member 24 to preload the sleeve member 24 against one of these stops 44, 45. In particular, one stop 44 is provided by the housing 3 and the other stop 45 is provided by the actuator 5. When the actuator 5 approaches its end position, the sleeve member 24 contacts the stop 44 at the housing 3. When the actuator 5 is further moved towards its end position, the snap feature 35 is compressed. Thereby, the snap feature 35 is caused to snap, thereby creating an audible click. In particular, a clear audible and tactile feedback may be provided to a user at the end of a dispense operation. After a dispense operation, when the user releases the actuator 5, the snap feature 35 may relax to its un-compressed form. When the snap feature 35 relaxes, it may create a further audible and tactile feedback.

In the shown embodiment, the axially moveable member 50, in particular the sleeve member 24 comprises an enhancement feature 51. The enhancement feature 51 comprises a rigid section 37 and a flexible section 36. The rigid section 37 is arranged at a distal end of the sleeve member 24, and the flexible section 36 is arranged at a proximal end of the sleeve member 24. The flexible section 36 comprises at least one opening 38. In particular, the flexible section 36 comprises three openings 38. Furthermore, the flexible section 36 comprises at least one, in particular three flexible arms 41. The flexible arms 41 are configured to elastically deflect when a compressing force is exerted on the sleeve member 24 in an axial direction. In an alternative embodiment, the flexible arms 41 could extend radially inwards to use the internal volume of the sleeve member 24 more effectively. In particular, the sleeve member 24 is compressed when a force is exerted on the sleeve member 24 in axial direction. Thereby, the sleeve member 24 acts as a spring member.

Furthermore, the flexible section 36 comprises a terminal ring 42. The terminal ring 42 connects the flexible arms 41. The terminal ring 42 comprises a contact face 43, which is configured to contact the snap feature 35, at least at the end of a dispense operation. Alternatively, the contact face 43 may comprise several points of contact with the snap feature. Thereby, a constraint on the vibration of the snap feature 35 may be reduced. Thereby, the audible and tactile feedback may be increased. In an alternative embodiment, the flexible arms 41 could be free-standing at the proximal end of the sleeve member 24. In this case, the contact surface 43 would be located at the free ends of the flexible arms 41.

As described above, the sleeve member 24 contacts the stop 44 at the housing 3 when the actuator 5 approaches its end position during a dispense operation, in particular when the actuator 5 interacts with the feedback feature 2. When the actuator 5 is further moved towards its end position, the snap feature 35 and the flexible section 36 of the sleeve member 24 are compressed at the same time. When the snap feature 35 is compressed above a certain load, its stiffness reduces rapidly. This will cause the flexible section 36 of the sleeve member 24 to expand rapidly and fully compress the snap feature 35. Thereby, the snap feature 35 is caused to snap, thereby creating an audible click. In particular, a clear audible and tactile feedback may be provided to a user at the end of a dispense operation. The tactile feedback comprises vibration and motion of the actuator 5, which is transmitted to a user, for example to a user's finger. Due to the low mass of the sleeve member 24 and the snap feature 35 and a relatively large amount of elastic energy stored within them, the resulting feedback may be louder and more energetic compared to an embodiment with a completely rigid sleeve member 24.

The flexibility of the sleeve member 24 may also improve the strength of the feedback by reducing the stiffness of the contact constraints on the snap feature 35. The contact constraints on the snap feature 35 are the constraints which limit a movement or vibration of the snap feature 35. This may allow the snap feature 35 to vibrate with a larger amplitude and for a longer duration by reducing the energy transmission to the contact components, compared to an embodiment with a completely rigid sleeve member 24. This results in more energy transmission to the air and a louder feedback.

When the load which is exerted on the snap feature 35 by the sleeve member 24 is released after a dispense operation, the snap feature 35 snaps back into its uncompressed form. Thereby, the snap feature 35 may create a further audible and tactile feedback. The sleeve member 24 also relaxes and turns back to its uncompressed form.

Figure 5:
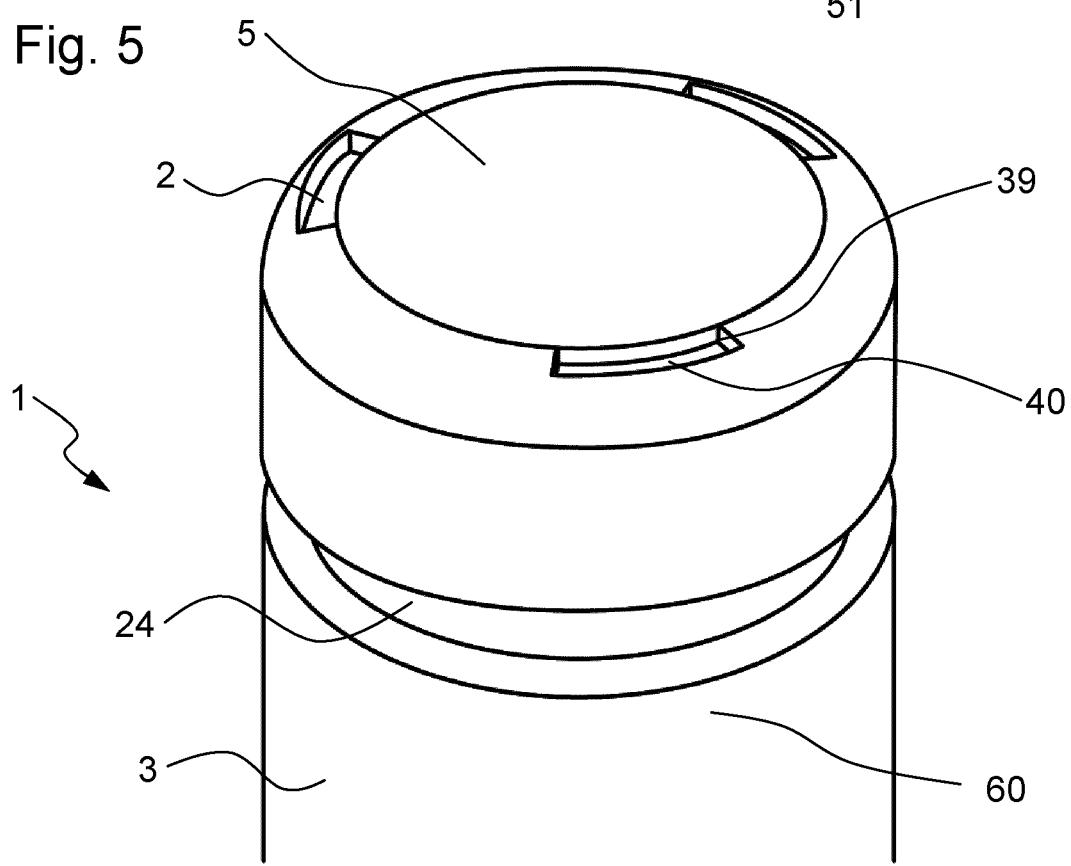
FIG. 5 shows a proximal section of a further embodiment of a drug delivery device.

FIG. 5 shows a proximal part of a drug delivery device 1 comprising a different embodiment of a feedback feature 2. In this embodiment, the actuator 5 comprises at least one, in particular three openings 39. The openings 39 are arranged at a proximal surface of the actuator 5. The feedback feature according to this embodiment comprises at least one tactile feature 40. In particular, the number of tactile features 40 corresponds to the number of openings 39 in the actuator. The tactile features 40 are configured as protrusions. The tactile features 40 are arranged at the axially moveable member 50, in particular at the sleeve member 24. In particular, the tactile features 40 may be an integral part of the sleeve member 24. In the embodiments shown in FIGS. 5 to 7, the sleeve member 24 is a fully rigid member. In an alternative embodiment, the sleeve member 24 may comprise a flexible section and a rigid section, according to the sleeve member 24 described with reference to FIG. 4. Thereby, the speed with which the tactile features 40 extend and hit the skin of a user may be increased. Thereby, the tactile feedback may be strong and well-defined.

Figure 6:
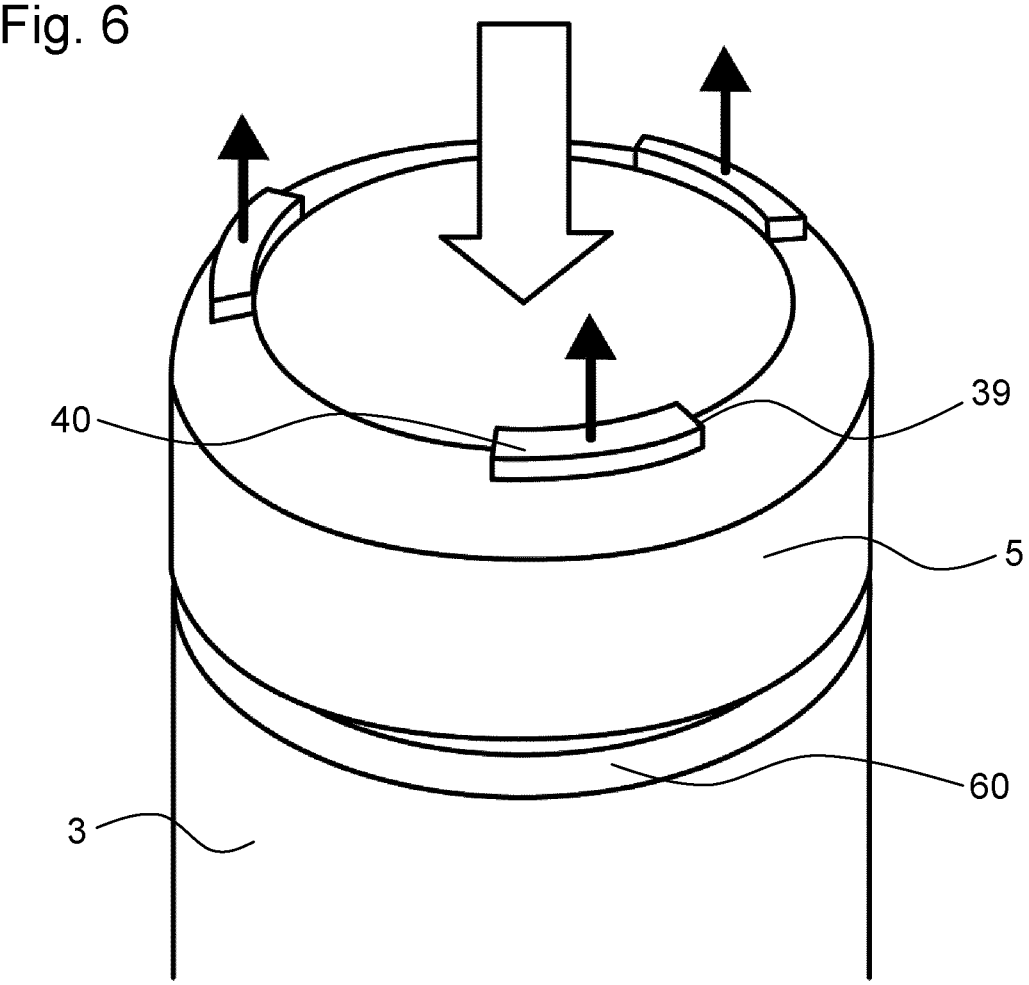
FIG. 6 shows the embodiment of FIG. 5 in a different state.

FIG. 6 shows a proximal part of the drug delivery device according to FIG. 5 when the actuator 5 is actuated. In particular, the actuator 5 is in its end position after a dispense operation. The end position of the actuator 5 may be its most distal position. In particular, the actuator 5 is in its end position when it is fully depressed. When the actuator 5 is moved in a distal direction and approaches its end position, the protrusions of the tactile features 40 are configured to move through the openings 39 of the actuator 5. Thereby, the tactile features 40 protrude from the drug delivery device 1, in particular from the actuator 5. Thereby, the tactile features 40 give a tactile feedback to a user at the end of a dispense operation. In particular, during a dispense operation a user may feel the feedback feature 2 protruding from the actuator 5, for example with the thumb.

Figure 7:
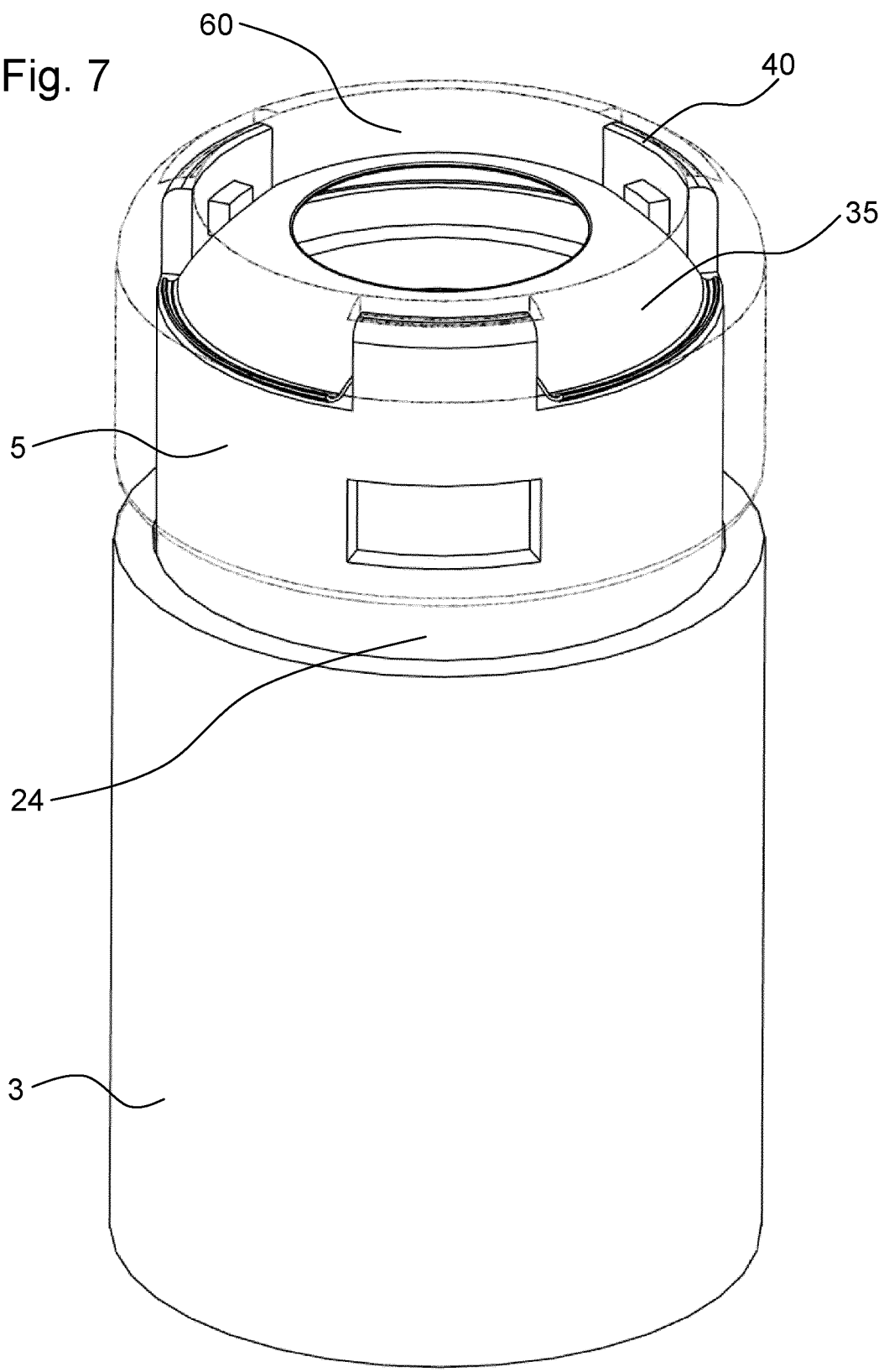
FIG. 7 shows the embodiment of FIG. 5 with the actuator shown transparent.

FIG. 7 shows a schematic view of a proximal part of a drug delivery device. The actuator 5 is shown transparent for a better understanding of the mechanism. The drug delivery device 1 comprises a snap feature 35, as described with reference to FIGS. 2 and 3. The tactile features 40 extend through the recesses 34 of the snap feature 35. When the snap feature 35 snaps through, the actuator 5 rapidly moves in a direction towards the dispensing end of the device. Thereby, the tactile features 40 rapidly protrude through the openings 39 provided by the actuator 5. Thereby, the tactile features 40 directly impact on the skin of a user. Thereby, a well defined tactile feedback is given to a user. This tactile feedback improves the clarity of a signal, especially in noisy environments or for users with hearing impairment.

Figure 8:
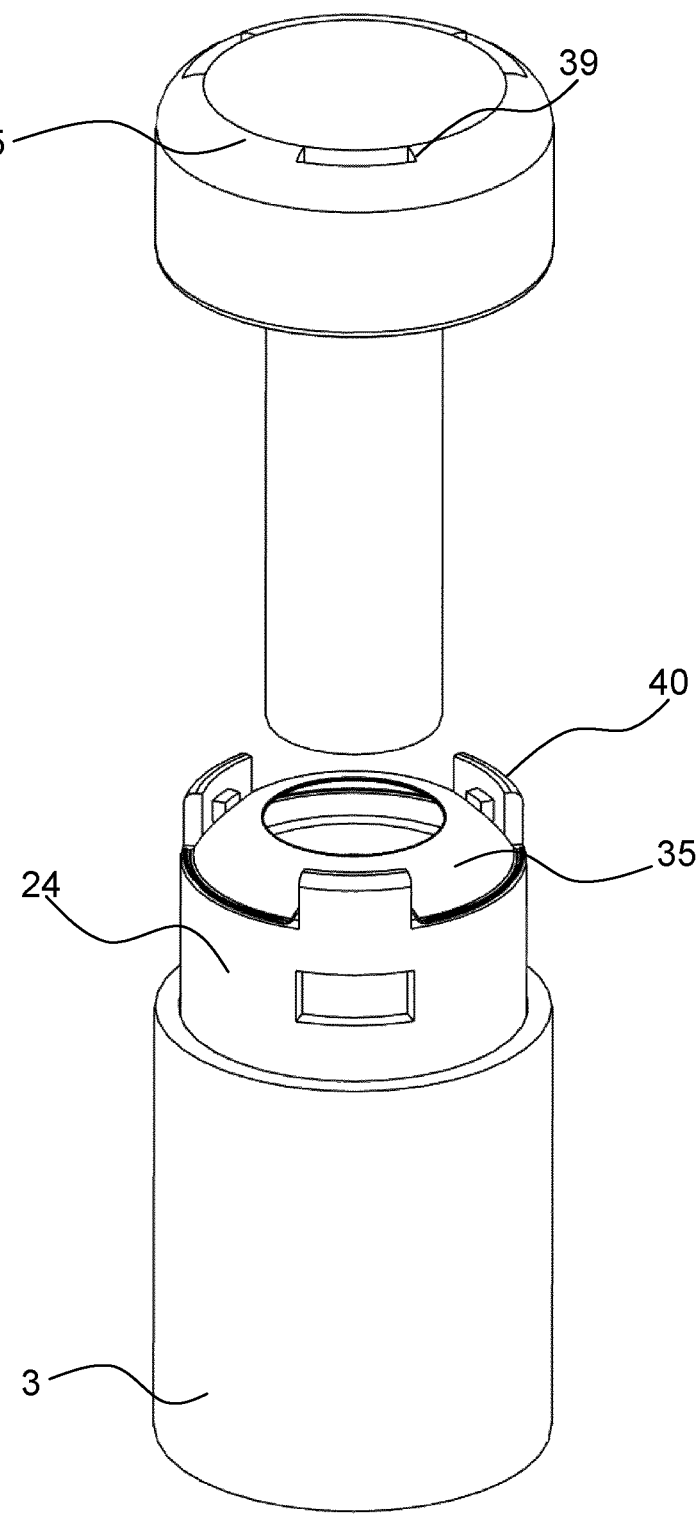
FIG. 8 shows the embodiment of FIG. 5 with the actuator being offset from the device.

In FIG. 8, the proximal part of the drug delivery device as shown in FIG. 7 is shown with the actuator 5 being offset from the device.

The invention claimed is:

1. An assembly for a drug delivery device, the assembly comprising:
an actuator configured to be operated to dispense a dose, wherein the actuator comprises a proximal member forming a button surface adapted to be directly operated by a user to initiate a dispense operation;
at least one feedback feature configured to indicate an end of the dispense operation to the user by giving feedback, the feedback comprising at least one of an audible or tactile feedback, and the at least one feedback feature comprising at least one snap feature which is configured to snap through when compressed above a certain load, thereby providing the feedback, wherein the at least one snap feature comprises a shape of a dome or a shape of an arched disc, and wherein the at least one snap feature is separate from and distally located relative to the proximal member of the actuator; and
an enhancement feature configured to enhance the feedback of the at least one feedback feature.

2. The assembly according to claim 1, wherein the enhancement feature is configured to increase an audibility of the audible feedback or to increase a tactility of the tactile feedback or to enhance an audible feedback by providing an additional tactile feedback or enhance a tactile feedback by providing an additional audible feedback.

3. The assembly according to claim 1, comprising an axially moveable member configured to move axially during an initial phase of the dispense operation, wherein the enhancement feature is attached to or is an integral part of the axially moveable member.

4. The assembly according to claim 1, wherein the at least one snap feature comprises an opening, wherein the actuator extends through the opening.

5. The assembly according to claim 4, wherein the at least one snap feature is configured to be compressed between the actuator and an axially moveable member.

6. The assembly according to claim 3, wherein the axially moveable member comprises a rigid section and a flexible section, and wherein the axially moveable member is configured to expand in an axial direction when the at least one snap feature snaps through.

7. The assembly according to claim 6, wherein expansion of the axially moveable member causes a full compression of the at least one snap feature to increase the feedback given by the at least one snap feature.

8. The assembly according to claim 1, wherein the at least one feedback feature comprises a metal material.

9. The assembly according to claim 1, wherein the at least one feedback feature comprises at least one tactile feature which is configured to give the tactile feedback to the user at the end of the dispense operation.

10. The assembly according to claim 9, wherein the at least one tactile feature is configured to protrude from the actuator at the end of the dispense operation.

11. The assembly according to claim 9, wherein the at least one tactile feature is configured to snap out when the at least one snap feature snaps through.

12. A drug delivery device comprising:
an assembly comprising:
an actuator configured to be operated to dispense a dose, wherein the actuator comprises a proximal member forming a button surface adapted to be directly operated by a user to initiate a dispense operation;
at least one feedback feature configured to indicate an end of the dispense operation to the user by giving feedback, the feedback comprising at least one of an audible or tactile feedback, and the at least one feedback feature comprising at least one snap feature which is configured to snap through when it is compressed above a certain load, thereby providing the feedback, wherein the at least one snap feature comprises a shape of a dome or a shape of an arched disc, and wherein the at least one snap feature is separate from and distally located relative to the proximal member of the actuator; and
an enhancement feature configured to enhance the feedback of the at least one feedback feature.

13. An assembly for a drug delivery device, the assembly comprising:
an actuator configured to be operated to dispense a dose, wherein the actuator comprises a proximal member forming a button surface adapted to be directly operated by a user to initiate a dispense operation;
at least one feedback feature configured to indicate an end of the dispense operation to a user by giving feedback, the feedback comprising at least one of an audible or tactile feedback, the at least one feedback feature comprises at least one tactile feature configured to protrude through an opening at the end of the dispense operation such that the at least one tactile feature contacts skin of a user, the opening being located in the proximal member of the actuator; and
an enhancement feature configured to enhance the feedback of the at least one feedback feature.

* * * * *